United States Patent [19]

Bisaccia et al.

[11] Patent Number: 5,219,882
[45] Date of Patent: Jun. 15, 1993

[54] TREATMENT METHODS FOR LYMES DISEASE AND ASSOCIATED DEBILITATING CONDITIONS

[76] Inventors: Emil Bisaccia, 4 Sunnybrook Rd., Basking Ridge, N.J. 07920; Albert S. Klainer, 315 W. 70th St., New York, N.Y. 10023

[21] Appl. No.: 781,962

[22] Filed: Oct. 24, 1991

[51] Int. Cl.$^5$ ............................................. A61K 31/35
[52] U.S. Cl. ................................................. 514/455
[58] Field of Search ....................................... 514/455

[56] References Cited

U.S. PATENT DOCUMENTS 4,999,375  3/1991  Bachynsky et al. ................ 514/455

OTHER PUBLICATIONS

Chemical Abstracts 95: 636y (1981).
Chemical Abstracts 114: 20282u (1991).
"Lyme Disease Vaccine May be Difficult to Develop Because of Immune Response to Vaccine Proteins", FDC Reports, The Blue Sheet, pp. 7-8, Jun. 10, 1992.

*Primary Examiner*—Leonard Schenkman
*Attorney, Agent, or Firm*—Bryan Cave

[57] ABSTRACT

A method is provided for treating human patients who have Lymes disease by using a psoralen compound, preferably administered in a dosage of 0.3 to 0.7 mg/kg, and activating same either in vitro or in vivo using electromagnetic radiation of a prescribed activating wavelength. The activation of the psoralen compound in the presence of a blood fraction from a patient suffering from Lymes disease produces a composition which will stimulate an effective immune response to the Lymes disease on the part of the patient.

10 Claims, No Drawings

TREATMENT METHODS FOR LYMES DISEASE AND ASSOCIATED DEBILITATING CONDITIONS

FIELD OF THE INVENTION

The present invention relates to the treatment of Lymes disease and associated debilitating conditions using photoactivateable compounds such as psoralens and activating electromagnetic radiation to engender a therapeutic immune response.

BACKGROUND OF THE INVENTION

Lymes disease is caused by a tick-borne spirochete. Early symptoms of Lymes disease which appear in weeks to months following initial infection include meningitis, facial palsy and migratory muscular-skeletal pain. Later appearing symptoms which can occur months to years after initial infection include chronic arthritis, encephalopathy, polyneuropathopy and leukoencephalitis. The usual therapy for Lymes disease is a 10-20 day course of antibiotics which must be implemented during the early stages of infection in order to have any appreciable expectation of success. However, even with early intervention, in a small percentage of patients the antibiotic therapy will be ineffective. This is particularly so if the spirochete has spread to the patient's nervous system.

Untreated patients, patients who did not receive antibiotic therapy early enough, or the small percentage of patients who did receive antibiotic therapy but nevertheless failed to respond, will generally experience the symptoms noted above as well as disturbances of memory, mood or sleep, axonal polyneuropathy with paresthesias or spinal pain. Typically, patients, particularly initially untreated patients, may also experience large knee effusions. The foregoing conditions associated with Lymes disease generally cannot be alleviated by late intervention with antibiotics.

Fortunately, it has now been discovered that untreated symptomatic patients as well as patients who received antibiotic therapy for Lymes disease but failed to respond, can be effectively treated using the photopheresis methods described below.

BRIEF DESCRIPTION OF THE INVENTION

In accordance with the present invention a method has been found for treating patients who are afflicted with Lymes disease and associated debilitating conditions using a photoactive compound that binds to nucleic acid upon activation by exposure to electromagnetic radiation of a prescribed spectrum, such as ultraviolet light. Psoralen compounds are particularly preferred for this purpose, especially the compound 8-methoxypsoralen—in which case UVA radiation is preferred for activating said compound.

In accordance with the invention, a photoactive compound such as 8-methoxypsoralen is administered to the patient's blood, or some fraction thereof, in vitro or in vivo using conventional administration routes. A portion of the patient's blood is then treated (preferably, extracorporeally) using photopheresis, which comprises subjecting the blood to electromagnetic radiation in such wavelengths suitable for activating the photoactive compound, such as ultraviolet light, preferably long wavelength ultraviolet light in the wavelength range of 320 to 400 nm, commonly called UVA light. The treated blood, or a fraction thereof, is returned to the patient (in the case of extracorporeal photopheresis) or remains in the patient (following in vivo photopheresis).

DETAILED DESCRIPTION OF THE INVENTION

While it is not intended that the scope of the present invention be limited by any specific theory of operation, it is believed that infections, particularly those which are not controlled by the normal immunological response of a patient, can be treated using a photopheresis treatment according to the invention. The herein described treatment is also believed by the inventors to (i) restore the ability of a treated patient's immune system to combat other infections, and (ii) restore the immune system's anamnestic response to previous infections.

In accordance with the photopheresis methods of the invention, treated infected cells as well as killed and/or attenuated pathogen, peptides, native sub-units of the pathogen itself (which are released upon cell break-up and/or shed into the blood) and/or pathogenic noninfectious pathogens may be used.

Mutation of the pathogen does not shield it from attenuation/inactivation during photopheresis and consequent generation of an immune response to the mutant forms of the pathogen. Thus, the treatment methods according to the invention provide a dynamic autogenous vaccine against infection.

The invention methods are also useful in the treatment of patients having an abnormally low white blood cell count.

According to the claimeds methods, a photoactive compound is first administered to the blood of an infected patient. The photoactive compound may be administered in vivo (e.g., orally or intravenously) or may be administered in vitro to a portion of the patient's blood which has been removed from the patient by employing conventional blood withdrawal techniques.

In accordance with the present invention, the photoactive compound selected should preferably be one that binds to the cell membrane of the pathogen and/or infected cells (e.g., by binding to a receptor and/or a nucleic acid fragment on the cell membrane) and/or to a nucleic acid in the cell nucleus or cell cytoplasm upon activation by exposure to electromagnetic radiation of a prescribed spectrum, such as ultraviolet light, for the purpose of inactivating and/or attenuating the pathogen and permitting the so treated pathogen and/or infected cells to be presented to the immune system of the patient. Psoralen compounds are particularly preferred for this purpose, especially the compound 8-methoxypsoralen—in which case UVA radiation is preferred for activating said compound.

Next, the portion of the patient's blood to which the photoactive compound has been administered is treated by subjecting the portion of the blood to photopheresis using said electromagnetic radiation—for example, ultraviolet light. The photopheresis step is preferably carried out in vitro using an extracorporeal photopheresis apparatus.

The photopheresis step in accordance with the present invention may also be carried out in vivo (PUVA).

A presently preferred extracorporeal photopheresis apparatus for use in the methods according to the invention is currently manufactured by Therakos, Inc., Westchester, Pa. under the name UVAR. A description of the Therakos UVAR photopheresis apparatus may be found in U.S. Pat. No. 4,683,889, granted to R. L. Edelson on Aug. 14, 1987, the contents of which are hereby incorporated by reference in their entirety.

The exposure of blood to ultraviolet light in a photopheresis apparatus is within the ability of persons having ordinary skill in the art.

When the photopheresis step is carried out in vitro, at least a fraction of the treated blood, or the treated free isolated virus, is returned to the patient following the photopheresis treatment. Preferably, the treatment method described hereinabove is repeated at an interval of about once per week to about once every four weeks. Most preferably, the treatment methods described herein are administered on two successive days and repeated approximately once per month (i.e., the patient preferably receives two treatments every month).

In view of the disclosure contained herein, those persons who are skilled in the art will be able to adjust the treatment parameters—i.e., dosage of the photoactive compound and electromagnetic radiation, periodicity of treatment (e.g., monthly, weekly, etc.) and the number of treatments administered in each period (e.g., twice per month on two successive days)—depending on the condition of the patient and the patient's response to the treatment.

Preferred photoactive compounds for use in accordance with the present invention are compounds known as psoralens (or furocoumarins) which are described in U.S. Pat. No. 4,321,919 the disclosure of which is incorporated herein by reference in their entirety.

The preferred photoactive compounds for use in accordance with the present invention include the following"
  psoralen;
  8-methoxypsoralen;
  4,5'8-trimethylpsoralen;
  5-methoxypsoralen;
  4-methylpsoralen;
  4,4-dimethylpsoralen;
  4-5'-dimethylpsoralen; and
  4',8-methoxypsoralen The most particularly preferred photoactive compound for use in accordance with the invention is 8-methoxypsoralen.

The determination of an effective dosage is within the ability of persons having ordinary skill in the art.

The photoactive compound, when administered to the patient's blood in vivo is preferably administered orally, but also can be administered intravenously and/or by other conventional administration routes.

The preferred dosage of the photoactive compound is in the range of about 0.3 to about 0.7 mg/kg of body weight although larger or smaller doses may be employed. When the photoactive compound is administered in vitro to only a portion of the patient's blood or fraction thereof, it is within the ability of those skilled in the art to calculate a dosage which is equivalent to said range based upon the volume of treated blood or fraction thereof.

When administered orally, the photoactive compound should preferably be administered at least about one hour prior to the photopheresis treatment. The timing of administration may be adjusted up or down as needed depending on the bioavailability of the photoactive compound, its expected half-life, etc. If administered intravenously, the times would generally be shorter.

The photopheresis treatment in the treatment methods according to the invention is preferably carried out using long wavelength ultraviolet light (UVA) at a wavelength within the range of 320 to 400 nm. The exposure to ultraviolet light during the photopheresis treatment preferably has a duration of about three to four hours, although shorter or longer treatment periods may be used if desired.

Whatever the spectrum of electromagnetic radiation, the exposure of infected cells and/or pathogen thereto, following administration of the photoactive compound, should be of sufficient intensity/duration to effectively inactivate and/or attenuate the pathogen. The selection of an appropriate wavelength for photopheresis as well as the exposure, depending upon the photoactive compound being employed and the conditions of treatment (e.g., in vivo exposure or in vitro exposure), is within the ability of those skilled in the art in view of the present disclosure.

When the photoactive compound is 8-methoxypsoralen, it is preferred in accordance with the invention to utilize an exposure to UVA radiation of about 2 Joules/meter$^2$ based upon the surface area of the pathogen and infected cells undergoing treatment.

When the photopheresis treatment according to the invention is carried out in vivo, careful attention should be paid to controlling the maximum radiant exposure so as to avoid unnecessary injury to the patient. Methods for calculating maximum radiant exposure to ultraviolet light are known in the art and, therefore, shall not be described herein.

WORKING EXAMPLE

A male patient, roughly 47 years of age, having Lymes disease and arthritis (diagnosis based upon positive Lymes titer, severe arthritis and effusion of the right knee) and who failed to respond to multiple courses of antibiotic therapy, was treated in the following manner:

The patient received treatment employing an 8-MOP dosage of 0.6 mg/kg (two treatments on successive days) initially repeated every four weeks. After three to four courses of the treatment in accordance with the invention, the patient enjoyed a general sense of well-being and, in particular, his joint pain completely subsided so that he was able to exercise as normal. The patient was maintained on the foregoing course of therapy for ten months at which point the frequency of treatment was extended to one 2-day treatment every six weeks. This course of therapy was continued for four months at which point the frequency of treatment was extended to one 2-day treatment every eight weeks. It was found that expansion of the treatment frequency in this manner did not cause the patient to regress. The patient is now being treated every three months on two successive days.

Thus, it was found that the photopheresis treatment employed in this patient was able to relieve all of his debilitating symptoms which were consistent with an advanced state of Lymes infection while conventional antibiotic therapy was completely ineffective.

While the foregoing description has been provided to illustrate the present invention, the inventors intend the scope of their invention to be limited solely by the scope of the following claims.

We claim:

1. A method for treating a human patient infected with Lymes disease, said method comprising the steps of:

a. administering to the patient's blood a psoralen compound in an amount within the range of about 0.3 to 0.7 mg/kg of body weight;
b. treating at least a portion of the patient's blood to which the psoralen compound has been administered, said treatment comprising subjecting the portion of blood to photopheresis by activating the psoralen compound using electromagnetic radiation of a prescribed activating spectrum; and
c. introducing the treated portion of the patient's blood to the patient's immune system to stimulate an effective immune response against the Lymes disease.

2. The method of claim 1 wherein the administration of the psoralen compound is performed in vitro.

3. The method of claim 1 wherein administration of the psoralen compound is performed in vivo.

4. The method claim 2 wherein the photopheresis is conducted extra-corporeally and wherein said method further comprises the step of returning the treated portion of blood to the patient following step (b).

5. The method claim 3 wherein the photopheresis is conducted extra-corporeally and wherein said method further comprises the step of returning the treated portion of blood to the patient following step (b).

6. The method claim 1 wherein the psoralen compound is selected from the group consisting of psoralen, 8-methoxypsoralen, 4,5',8-trimethylpsoralen, 5-methoxypsoralen, 4-methylpsoralen, 4,4-dimethylpsoralen, 4,5'-dimethylpsoralen and 4',8-dimethylpsoralen.

7. The method of claim 6, wherein the psoralen compound is selected from the group consisting of 8-methoxypsoralen, psoralen, and 4,5',8-trimethylpsoralen.

8. The method of claim 7, wherein the psoralen compound is 8-methoxypsoralen.

9. The method of claim 8, wherein the 8-methoxypsoralen is administered in a dosage of about 0.3 to about 0.7 mg/kg.

10. The method of claim 8, wherein steps (a), (b) and (c) are performed on two successive days, said steps (a), (b) and (c) being performed on the first day and repeated on the following day, at an interval of between about one to four weeks between each such 2-day treatment.

* * * * *